(12) United States Patent
Hollabaugh et al.

(10) Patent No.: US 11,927,393 B2
(45) Date of Patent: Mar. 12, 2024

(54) FIBER SLURRY TRAY AND PROCESS

(71) Applicant: DCI Donor Services, Inc., Nashville, TN (US)

(72) Inventors: Stephen Hollabaugh, Nashville, TN (US); Chris Cowan, Nashville, TN (US)

(73) Assignee: DCI Donor Services, Inc., Nashville, TN (US)

( * ) Notice: Subject to any disclaimer, the term of this patent is extended or adjusted under 35 U.S.C. 154(b) by 491 days.

(21) Appl. No.: 17/246,340

(22) Filed: Apr. 30, 2021

(65) Prior Publication Data

US 2021/0341225 A1 Nov. 4, 2021

Related U.S. Application Data

(60) Provisional application No. 63/018,275, filed on Apr. 30, 2020.

(51) Int. Cl.
| | |
|---|---|
| *F26B 5/06* | (2006.01) |
| *F26B 1/00* | (2006.01) |
| *F26B 25/18* | (2006.01) |
| *A61L 27/38* | (2006.01) |

(52) U.S. Cl.
CPC ............... *F26B 5/06* (2013.01); *F26B 1/00* (2013.01); *F26B 25/185* (2013.01); *A61L 27/3847* (2013.01)

(58) Field of Classification Search
CPC .. F26B 5/06; F26B 1/00; F26B 25/185; A61L 27/3847

USPC ............................................. 34/92, 287
See application file for complete search history.

(56) References Cited

U.S. PATENT DOCUMENTS

| | | | | |
|---|---|---|---|---|
| 5,507,813 | A * | 4/1996 | Dowd .................. | A61L 27/3683 623/23.63 |
| 6,447,701 | B1 * | 9/2002 | Heschel .................. | A61L 27/56 264/28 |
| 6,863,900 | B2 * | 3/2005 | Kadiyala ............. | A61L 27/3821 523/114 |
| 8,551,505 | B2 * | 10/2013 | Boyden ..................... | F26B 5/06 424/1.29 |
| 9,526,770 | B2 * | 12/2016 | Tseng ..................... | A61K 33/06 |
| 11,511,016 | B2 * | 11/2022 | Le Visage ........... | C08B 37/0054 |
| D977,672 | S * | 2/2023 | Hollabaugh ................ | D24/224 |
| 2010/0161074 | A1 * | 6/2010 | McKay ............... | A61L 24/0015 623/23.5 |
| 2021/0341225 | A1 * | 11/2021 | Hollabaugh ........ | A61L 27/3608 |

FOREIGN PATENT DOCUMENTS

| | | | | | |
|---|---|---|---|---|---|
| CN | | 114401697 A | * | 4/2022 | ......... A61L 27/3608 |
| JP | | 2010512846 A | * | 4/2010 | |
| WO | WO-2021050901 A1 | * | 3/2021 | ......... A61L 27/3608 |

* cited by examiner

*Primary Examiner* — Stephen M Gravini
(74) *Attorney, Agent, or Firm* — Stites & Harbison PLLC; Richard S. Myers, Jr.

(57) ABSTRACT

A method for processing demineralized bone fibers, comprising a centrifuging step, and following the centrifuging step hydrated in sterile water to create a slurry; providing a tray to receive said fiber slurry; freezing the tray and fiber slurry; and lyophilizing the fiber slurry to create dried fibers.

18 Claims, 5 Drawing Sheets

FIBER SLURRY TRAY AND PROCESS

PRIOR APPLICATIONS

This application claims benefit to U.S. Application No. 63/018,275, filed Apr. 30, 2020; the contents of which are incorporated herein by reference in their entirety.

FIELD OF THE INVENTION

Generally, the present invention relates to a lyophilization process used to process tissue fibers. In certain embodiments of the present invention, the tissue fibers are allograft bone fibers.

The present invention also relates to a fiber slurry tray with removable baffles that is used in a fiber lyophilization process.

BACKGROUND OF THE INVENTION

The process of lyophilization, sometimes referred to as freeze drying is known in the art. This process includes an application of a physical phenomenon called sublimation: the transition of a substance from solid to a gaseous state, without first passing through the liquid phase. During lyophilization, the water in the frozen sample is removed as water vapor, without first thawing the sample. One common advantage to this process is that lyophilized samples may be stored much longer than untreated samples.

Lyophilization is largely applied to three industries: Pharmaceuticals, dehydrated food/drink, and human tissue. Lyophilization often involves the dehydration of solutions to create a product in the form of a hydratable powder. Typically, this is required because it would be impossible to make the molecules in a dry state. The molecules are created in an aqueous form and the lyophilized to completely dehydrate the product. Lyophilization is also used to dehydrate food for storage (fruits/veggie) or make powdered drink (coffee).

Lyophilization is also used to dehydrate human tissue to increase shelf stability at ambient temperatures. Typically, the goal is the remove water by centrifugal force and then lyophilize to remove the remaining water.

Thus, one embodiment of the present invention is a lyophilization process involving demineralized bone fibers.

Demineralized bone fibers, including the ones processed in the methods described herein, are useful in bone grafting procedures. The process of demineralizing bone is well known in the art, and involves mixing mineralized bone with acid in order to remove calcium from the tissue. It is useful because when calcium is removed, signaling molecules within the bone are "released," which leads to an increase in osteoinduction, a component of osteogenesis.

Bone grafts using the fibers of the present invention can help promote osteogenesis, the formation of new bone within the graft and osteoconduction, where a matrix often containing graft material acts as a scaffold on which bone and cells in the recipient are able to form. The scaffolds promote the migration, proliferation and differentiation of bone cells for bone regeneration.

The bone fibers of the present invention can be formed into various surgical implants as well as bone void fillers. Examples include strips, discs, screws, and other implants of various shapes. Bone void fillers are easily manipulated masses that may be utilized by a doctor to address a wide variety of bone defects. The implants may be used in general orthopaedic applications, trauma applications, and spinal applications, as well as for repair of craniomaxial defects, dental defects, and other bony defects.

The fibers of the present invention may be derived from, for example, the cortical component of the long bones of the femur, tibia, humerus, radius, ulna, and fibula, or other suitable long bones of a mammal. Typically, the cortical bone is first stripped of all soft tissue elements and then cleaned using detergents/surfactants to remove residual blood and lipids from the bone surface. The cleaned cortical bone is then processed into elongated particles using a milling process that results in fibers that have various ranges in sizes, thickness, and length. For example, they may range in size from about 10 µm to about 1000 µm in thickness, about 20 µm to about 20 cm in length and about 5 µm to about 1 cm in width. The cortical fibers are demineralized in dilute acid resulting in a residual calcium content ranging from less than 15% w/w for partially demineralized fibers, less than 8% w/w for demineralized fibers, and less than 1% w/w for substantially or fully demineralized fibers. The calcium content of the fully demineralized fibers may be negligibly small, such that the fibers consist essentially of collagen, non-collagen protein, including glycoproteins, growth factors, and other non-mineral substances found in the original bone, although not necessarily in their original quantities. In other embodiments of the present invention, blocks of cortical bone are demineralized, and the fibers are subsequently produced by crushing or shredding the demineralized blocks. As used herein, the term "demineralized" includes any level of demineralization.

Previously, Applicant and others demineralized cortical fibers by soaking in acid. Excess water was then removed by employing a centrifuge to remove excess water. Fibers were then manipulated by hand to prepare them for lyophilization. The goal was to tease the fibers apart without breaking them. If too many fibers were packed too closely together, fibers would become hard and rigid after lyophilization. This process was very technician dependent. Final fiber outcome was based on technician skill and care.

For example, inadequate manipulation before lyophilization would necessitate more hand manipulation after lyophilization in order to break about clumping. This breaks fiber length down. Fibers were no longer long and fluffy, two very desirable characteristics. Additionally, this requires more time at packaging. Also, fibers that needed to be manipulated excessively at packaging may break down to a point that they were out of specification.

Thus, there is a long felt need for a process for producing demineralized cortical fibers that is more effective and does not have the disadvantages discussed above.

SUMMARY OF THE INVENTION

As stated above, one embodiment of the present invention is a novel lyophilization process used to process tissue fibers.

Another embodiment of the invention is a fiber slurry tray used as part of a lyophilization process.

Another embodiment of the present invention is a method of treating demineralized bone fibers, comprising a centrifuging step and a following hydration step.

Another embodiment of the present invention is a method of processing demineralized bone fibers, comprising manipulating fibers in a fiber slurry tray following hydration.

Another embodiment of the present invention is inserting baffles in the fiber slurry tray after manipulation.

Another embodiment of the present invention is a method for processing demineralized bone fibers that comprises providing demineralized bone fibers; centrifuging said demineralized bone fibers; following said centrifuging step, hydrating said demineralized bone fibers in sterile water to create a fiber slurry; providing a tray to receive said fiber slurry; freezing the tray and fiber slurry; lyophilizing the fiber slurry to create dried fibers; and removing the dried fibers from the tray.

In another aspect, the hydrating step is in a separate container than the tray, and following the hydrating step, the slurry is transferred to the tray.

In another aspect, the hydration step is conducted with sterile water. In one example, the ratio of fibers to sterile water is about 0.1:1 (fibers(g):water(g)) to about 0.3:1.

In another aspect of the invention, the fibers are manipulated in the tray to separate fiber clumps.

In yet another aspect, the depth of the slurry in the tray is about 15 mm or less.

In another aspect, the tray comprises at least one baffle that transverses the tray. In another aspect, the baffle is removable and the baffle is inserted into the tray after the tray receives the slurry.

In another aspect, the tray is about 9-12 inches×9-12 inches, and the slurry is up to 150 grams of fibers in about 400-700 cc of sterile water.

Another embodiment of the present invention is a method of processing demineralized bone fibers, that comprises providing demineralized bone fibers; hydrating the fibers in sterile water to create a slurry; providing a tray to receive said fiber slurry; and manipulating said fibers in the tray to separate fiber clumps. The tray is generally square or rectangular with two sides and two ends; and at least one baffle traversing the tray.

In one aspect, the side walls comprise a wing angled inward from the sides, the wing comprising a slot to receive and support a baffle.

In another aspect, the baffles are removable, and the baffles are inserted into the tray after the fiber slurry is introduced to the tray and manipulated.

In another aspect, the tray is generally square shaped and is about 9-12 inches×9-12 inches.

In another aspect, the wing has four shots and the tray has four removal baffles that are received and supported by the slots. The two opposed side walls may each have wings, and the baffle is supported by a slot on each wing. The tray and baffles may be stainless steel.

These and other embodiments will be apparent by this description and accompanying drawings.

BRIEF DESCRIPTION OF THE DRAWINGS

The accompanying figures, which are incorporated in and constitute a part of this specification, illustrate several aspects and together with the description serve to explain the principles of the invention.

DESCRIPTION OF EMBODIMENTS OF THE PRESENT INVENTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Before the present articles, systems, devices, and/or methods are disclosed and described, it is to be understood that they are not limited to specific synthetic methods unless otherwise specified, or to particular reagents or process steps unless otherwise specified, as such may, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As stated above, the Applicant has developed a process to overcome the disadvantages of prior fiber preparation processes.

In one embodiment of the present invention, demineralized fibers are prepared by being centrifuged to remove excess water. Preferably, the fibers are dry-spun for consistency. After the centrifuge step, the fibers are generally clumped together.

Following the centrifuge step, the fibers are added to sterile water for hydration, creating a fiber slurry. This hydration step allows for a variety of bone fiber characteristics. While one example is mixing about 0.1 g to about 500 g of centrifuged fibers with about 100 cc to about 1000 cc of sterile water. Additional ranges are about 0.1 g to about 300 g of centrifuged fibers with about 200 cc to about 800 cc of sterile water. Additional ranges are about 0.1 g to about 200 g of centrifuged fibers and about 400 cc to about 700 cc of sterile water. The ranges can be manipulated by one of ordinary skill in the art. The more sterile water that is added, the more "fluffy" the fibers will be. However by adding more water, the lyophilization time increases to diminishing returns. Less water may be added as well, but the ideal characteristics will diminish and the lyophilization time may decrease.

The fiber slurry is then moved to the fiber slurry tray of the present invention. The fibers are manipulated in the tray in order to suspend individual fibers separately from each other.

In one embodiment of the invention, the fibers are rehydrated in a container separate from the fiber slurry tray. In another embodiment, the fibers are rehydrated in the fiber slurry tray.

One of ordinary skill in the art would understand that by the term "manipulation" it is understand that the fibers in the slurry are handled in a relatively gentle manner in order to separate fibers that have clumped together and to evenly distribute the fibers throughout the tray. The trays are now prepared to be frozen and then proceed to the lyophilization process.

Following the lyophilization process, the fibers are removed from the slurry tray for storage.

After the lyophilization step, the fibers have a fluffy appearance and texture. As described herein, the process of the present invention creates fibers that more readily absorb solution during rehydration, and the process of the present invention creates longer fibers than the prior art methods.

The fiber to water ratio in the tray and slurry volume to surface area ratio can be varied greatly, and optimized as a tool to balance fiber properties and lyophilization time. If excess water is added, fibers may have better qualities. However, there is diminishing returns and the amount of water to be lyophilized impacts the cycle time of the lyophilization.

For example, a fiber slurry composed of fibers and sterile water may be added together at a rate (fibers(g):water(g)) of about 0.01:1.0 to about 2.0:1.0. In other embodiments, the rate is 0.1:1 to 0.3:1. In other embodiments, the rate is 0.2:1 to 0.3:1. A preferred ratio to balance final graft quality, bulk processing, and lyophilization cycle time is approximately a maximum of about 0.23:1.

The depth of the fiber slurry in the tray can vary. In embodiments of the present invention, the depth can be about 5-30 mm. In other embodiments, the depth is about 5-20 mm. In other embodiments, the depth is about 5-15 mm. Preferably, the depth is about 15 mm or less. Also, preferably, the depth is about 13 mm or less.

Another embodiment of the present invention is a fiber slurry tray. The tray comprises baffles, which decrease slushing of the fibers. When excess slushing of the slurry occurs, bunching of the fibers occurs. With the baffles, shushing is reduced.

Figure 1:
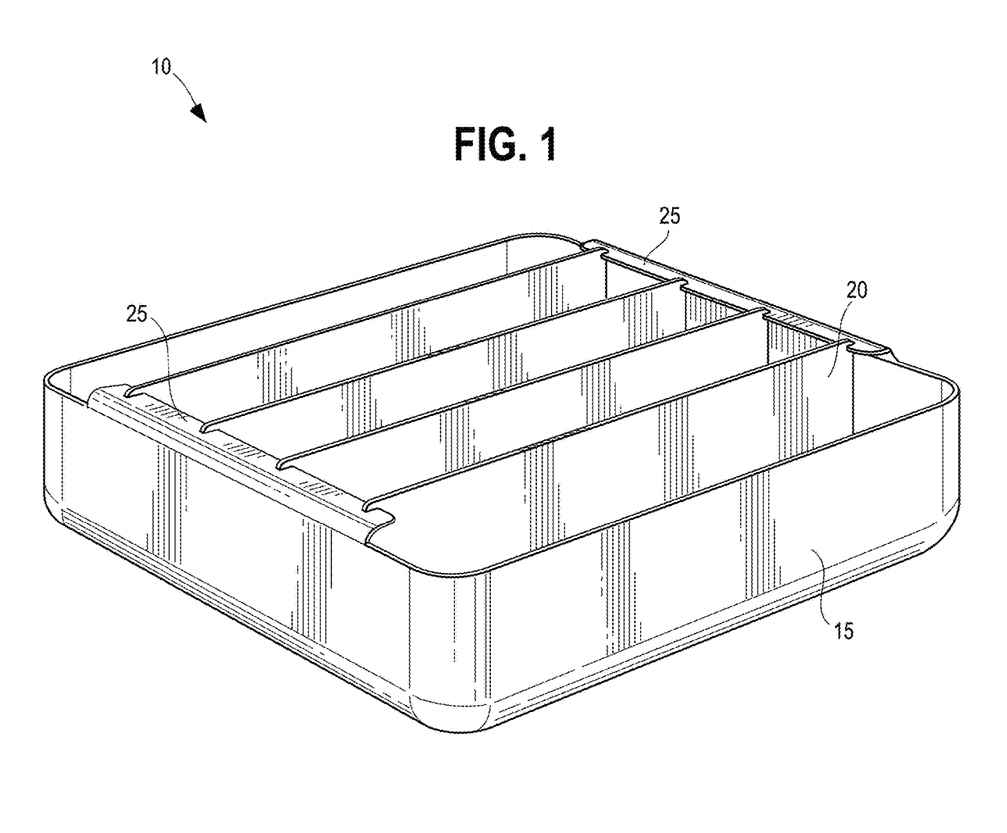
FIG. 1 shows a perspective view of a fiber slurry tray of the present invention.

One example of this embodiment is shown in FIG. 1. A fiber slurry tray 10 comprises an outer wall 15 and a floor (not shown in this figure). Preferably, the outer wall 15 generally forms a square or rectangle. In one embodiment, the outer wall 15 is in the general shape of a square that is about 5-24 inches×5-24 inches. In another embodiment, the outer wall 15 forms the general shape of a square that is about 9-12 inches×9-12 inches. Another example is 10.5 inches×10.5 inches.

The fiber slurry tray 10 of the present invention includes at least one baffle 20 traversing the tray. In some embodiments, the baffle 20 is fixed to the outer wall and perpendicular to the floor. In other embodiments, the baffle 20 is removable.

If the baffle 20 is removable and not permanently attached to the side walls, the tray 10 may comprise a wing 25 that includes a slot or grove to receive the baffles 20 and hold them perpendicular to the floor. FIG. 1 shows a tray 10 with four baffles 20. However, the number of baffles 20 can vary. Examples include trays 10 with two to ten baffles 20. Preferably, there is a baffle 20 for every 2-6 inches of fiber slurry.

Figure 2:
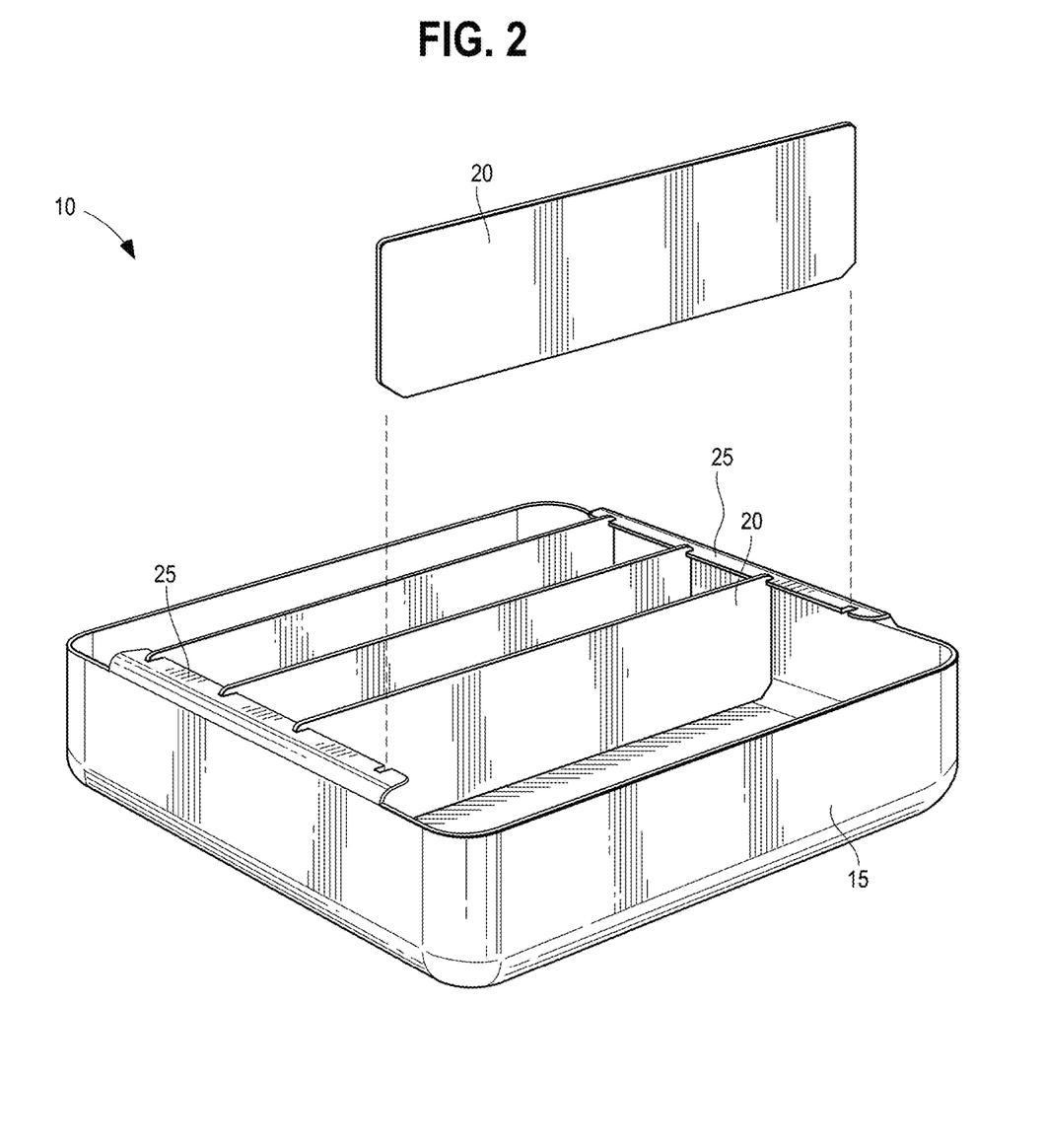
FIG. 2 shows a perspective view of a fiber tray of the present invention with one of the baffles removed.

FIG. 2 shows an additional view of a fiber slurry tray 10 of the present invention. The outer wall 15 and floor 17 are shown. Additionally, this embodiment comprises four baffles 20. The baffles 20 are received and supported by the wings 25 that have a slot 26 that engages the baffles 20 and holds them generally perpendicular to the floor 17. This tray 10 has removable baffles 20, and one is shown above the wings prior to insertion into the tray 10.

Figure 3:
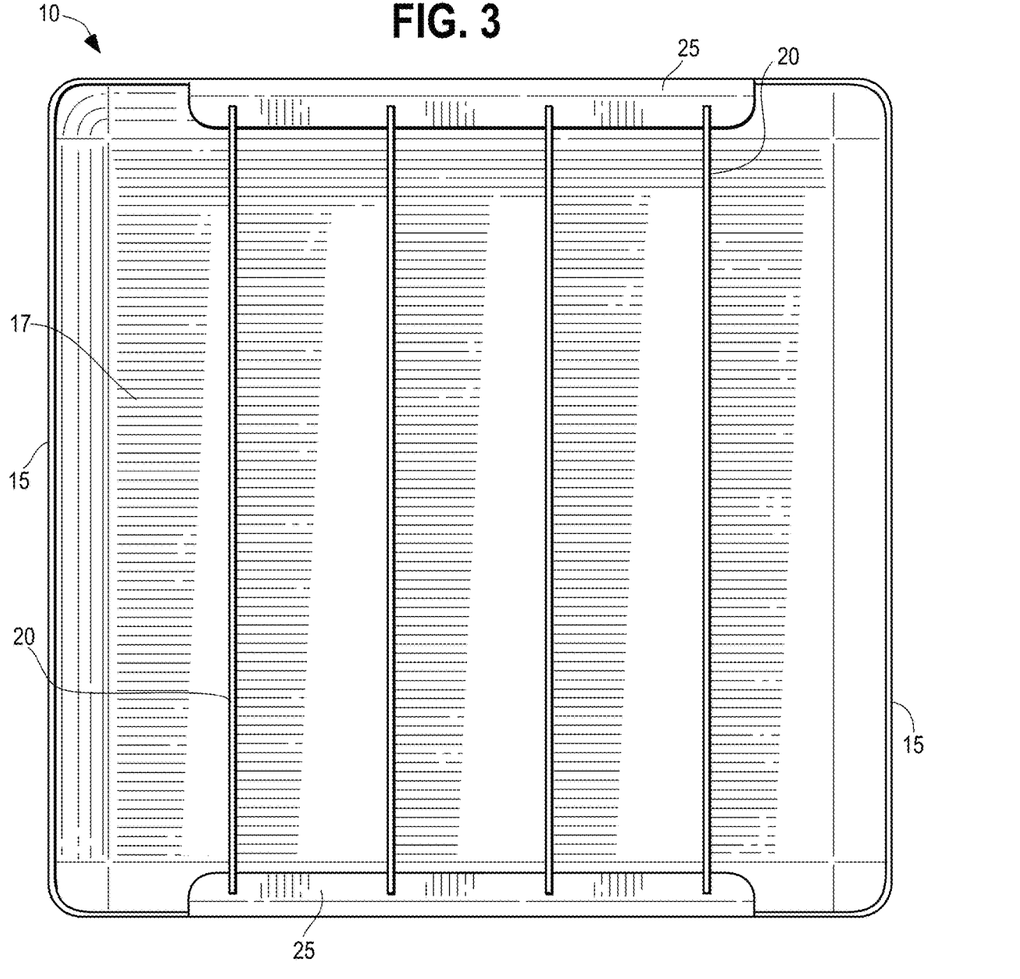
FIG. 3 shows a top view of a fiber slurry tray of the present invention.

FIG. 3 shows a top view of an embodiment of the slurry tray 10 of the present invention. As can be seen in this particular embodiment, the outer wall 15 is generally a square. Also, there are four baffles 20 that are supported by the outer wall wings 25 and held generally perpendicular to the floor 17.

Figure 4:
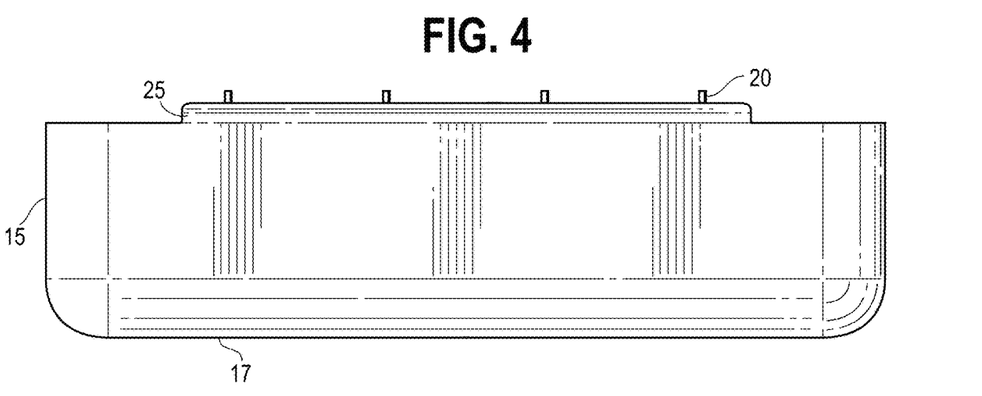
FIG. 4 shows a side view of a fiber slurry tray of the present invention.

FIG. 4 shows a side view of an embodiment of the present invention. Here, there are also four baffles 20 held by the outer wall wings 25. This view shows the bottom of the outer wall 15 being rounded as it meets the floor 17. The angle where the wall meets the floor is optional, and can vary from what is shown. For example, it may be sharper. With this embodiment, the baffles will also be curved or angled at the bottom to match the wall/floor angle.

FIG. 4 also shows an embodiment where the baffles 20 are taller than the outer wall 15. This allows them to be easily placed in the slot of the wings 26 and more easily removed from the tray.

The embodiment of the one-piece fiber slurry tray 10 with removable baffles 20 has been designed to improve fiber slurry process. Without being bound by theory or mechanism, the baffles have the functions of reducing motion of the fiber slurry before freezing. If there is excess fluid motion during the transportation to the freezer, fibers can build up in one portion of the tray. If fibers are concentrated in one portion of the tray, the fibers become self-insulating. This self-insulation reduces the heat transfer to the frozen water during the lyophilization process which inhibits the sublimation rate.

Also, the baffles provide added heat transfer through a larger portion of the fiber slurry mass which increases the sublimation rate that would otherwise be inhibited by the self-insulating properties of the fibers. Thus, while the tray and baffles may be made from a variety of materials, a preferred material is stainless steel. Stainless steel also aids in more effective cleaning.

The fiber slurry process of the present invention significantly reduces the correlation between technician skill/care and final fiber quality after lyophilization. The pre-lyophilization steps are faster and easier than previous methods.

Final lyophilized fibers require minimal manipulation during the packaging event. This reduces event time. Also, the process of the present invention also directly impacts the final fiber quality when compared to the previous process. For example, fibers produced with the process of the present invention are consistently longer. Additionally, fibers produced with the process of the present invention show significantly reduced clumping. Additionally, fibers produced with the process of the present invention are consistently more soft and fluffy. Additionally, fibers produced with the process of the present invention hydrate more quickly.

The process of the present invention shows superior and unexpected results compared to previous processes. Applicant has found that with the prior process, approximately 10% of loose fiber donors were rejected for fiber quality. This process of the present invention has reduced this rejection down to 0% for fiber length and clumping handling requirements. Furthermore all non-rejected fibers still retain better qualities when compared to fibers produced in the old process.

In one embodiment, the trays are made of one continuous welded piece of stainless steel (including a slotting feature to allow for removable baffles) to ensure easy decontamination, disinfection, and sterilization. In one embodiment, they include bent wings with slots to hold baffles in place. Additionally, separate baffles have been designed so that they can be added after fiber slurry addition and removed before lyophilized fiber packaging.

Figure 5:
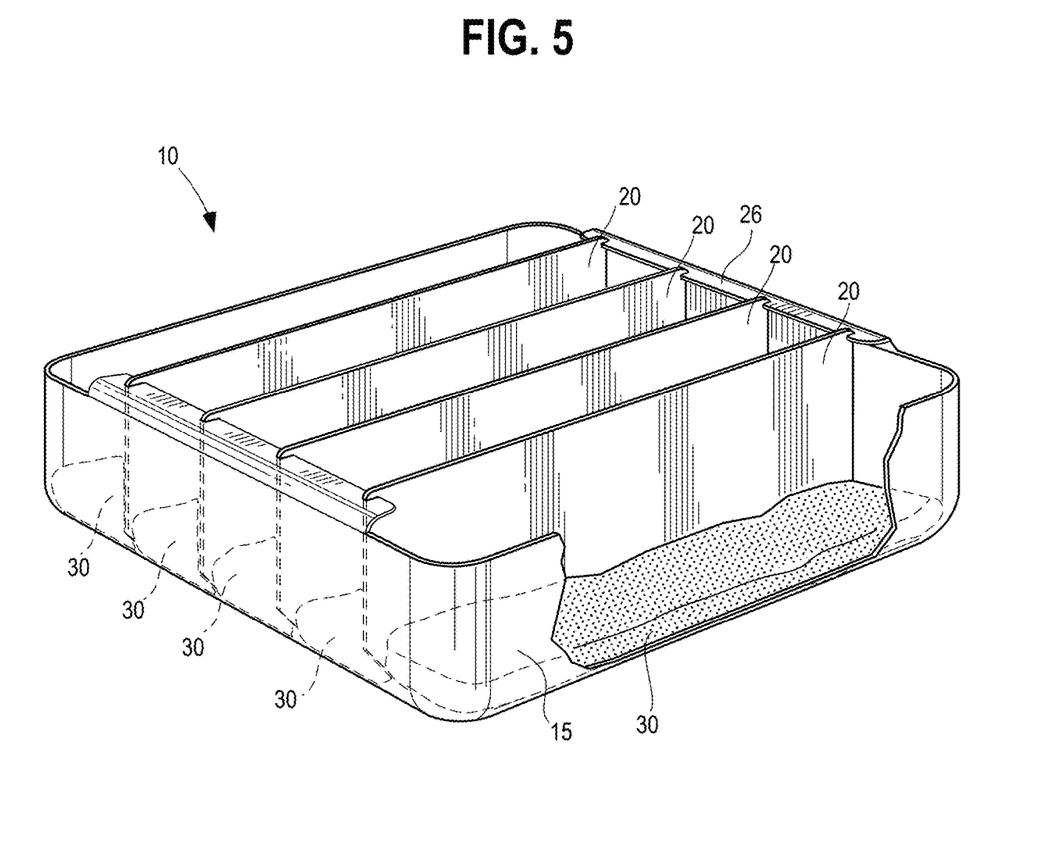
FIG. 5 shows a perspective of a fiber slurry tray of the present invention that includes a fiber slurry that is prepared for freezing.

FIG. 5 shows a fiber slurry tray of the present invention that contains a fiber slurry 30. As stated above, the baffles 20 prevent excessive motion of the slurry prior to freezing. Reduction of motion is highly advantageous because it reduces the tendency of clumping prior to the freezing step.

EXAMPLE

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

This example demonstrates a method of producing demineralized fibers that can be used in grafting procedures.

First, demineralized fibers are dry-spun in a centrifuge. Wet, demineralized fibers are placed in centrifuge cups, and are centrifuged at an RPM and for a length of time such that the maximum amount of water is removed. After removal from the centrifuge, the fibers are usually in one or two clumps.

The fibers are rehydrated. The water ratio will be calculated using dry-spun weight. The fibers are hydrated with an appropriate amount of sterile water and distributed between fiber trays for lyophilization. Up to 150 grams of demineralized fibers and 650 cc of sterile water will be added to a 10.5"×10.5" tray. The fibers (0-150 grams) are hydrated with 650 cc of sterile water in a container outside of the tray. This creates a fiber slurry from the clumps that were removed from the centrifuge.

After adding fiber slurry to the tray, fibers are gently manipulated in order to break up fiber clumps and evenly distribute across the tray. Baffles will then be installed in the tray. The trays are optionally sealed in a permeable pouch appropriate to maintain sterility and allow for lyophilization. The tray is them transferred to a freezer. The trays remain in freezer for at least approximately 8 hours. Once the slurry has have been fully frozen, they are ready for lyophilization. Following lyophilization, the fibers are removed from the trays and packaged.

Figure 6:
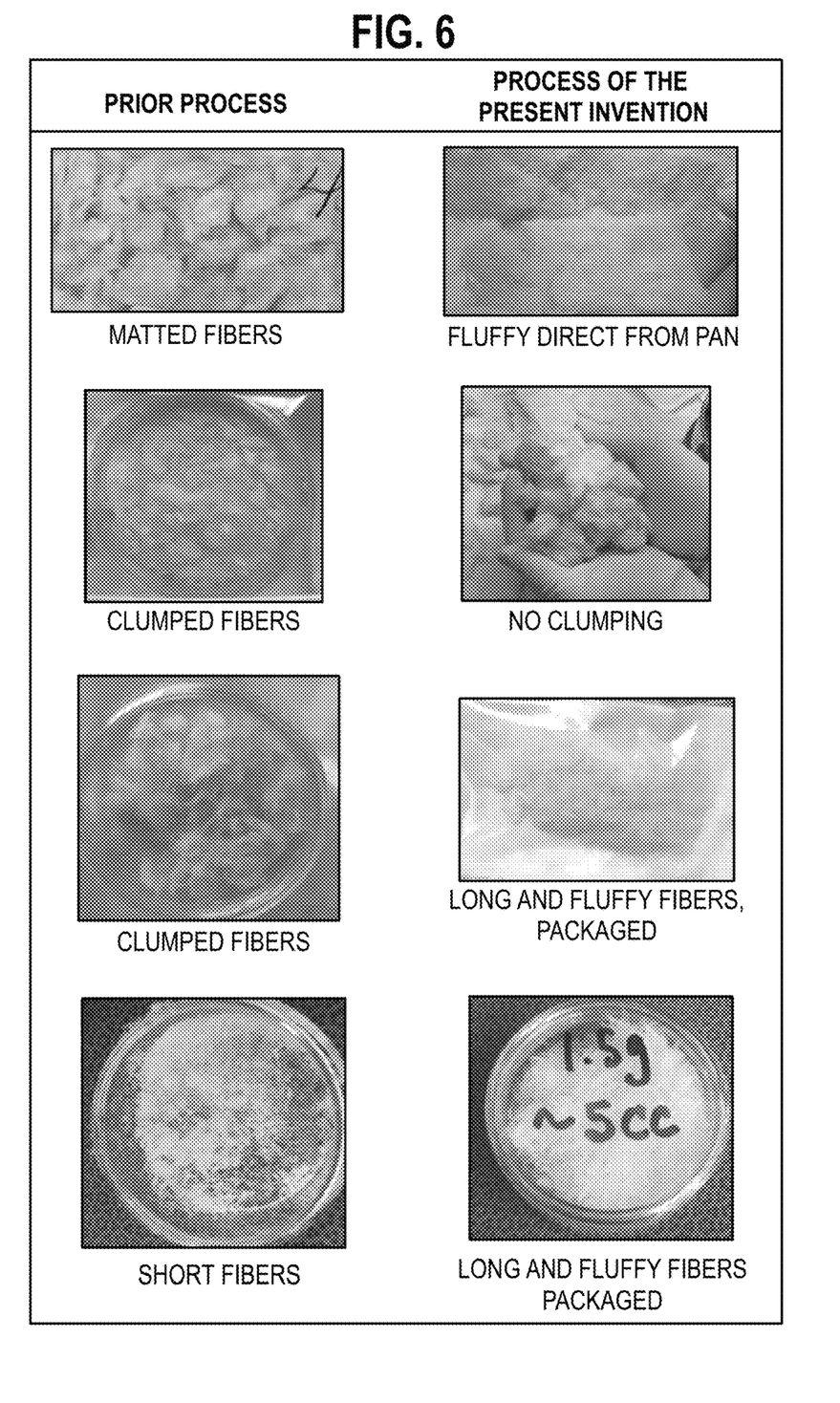
FIG. 6 is a table that shows some advantages of the present invention compared to a prior art process.

FIG. 6 compares fibers prepared with the process of the present invention. As can be seen by the comparison, the fibers prepared with the process of the present invention are superior in that they are longer and have important fluffy characteristics. The fibers prepared with the process of the present invention also exhibit less clumping. The process of the present invention allows for fluffy fibers compared to the previous process, where matted fibers are common. The fibers prepared with the process of the present invention have little to no clumping compared to the prior art process, where clumped fibers are common. Additionally, the process of the present invention allows for longer fibers compared to the prior art process.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

Unless otherwise indicated, all numbers expressing quantities of ingredients, properties such as reaction conditions, and so forth used herein are to be understood as being modified in all instances by the term "about." Accordingly, unless indicated to the contrary, the numerical parameters set forth in the herein are approximations that may vary depending upon the desired properties sought to be determined by the present invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

We claim:

1. A method for processing demineralized bone fibers, comprising:
   providing demineralized bone fibers;
   centrifuging said demineralized bone fibers;
   following said centrifuging step, hydrating said demineralized bone fibers in sterile water to create a fiber slurry;
   providing a tray to receive said fiber slurry;
   freezing the tray and fiber slurry;
   lyophilizing the fiber slurry to create dried fibers;
   removing the dried fibers from the tray.

2. The method of claim 1, wherein the hydrating step is in a separate container than the tray, and following the hydrating step, the slurry is transferred to the tray.

3. The method of claim 1, wherein the hydration step is conducted with sterile water.

4. The method of claim 1, wherein the fibers are manipulated in the tray to separate fiber clumps.

5. The method of claim 1, wherein the ratio of fibers to sterile water is about 0.1:1 (fibers(g):water(g)) to about 0.3:1.

6. The method of claim 1, wherein the depth of the slurry in the tray is about 15 mm or less.

7. The method of claim 1, wherein the tray comprises at least one baffle that transverses the tray.

8. The method of claim 7, wherein the baffle is removable and the baffle is inserted into the tray after the tray receives the slurry.

9. The method of claim 1, wherein the tray is about 9-12 inches×9-12 inches, and the slurry is up to 150 grams of fibers in about 400-700 cc of sterile water.

10. A method of processing demineralized bone fibers, comprising:
    providing demineralized bone fibers;

hydrating said fibers in sterile water to create a slurry;
providing a tray to receive said fiber slurry;
manipulating said fibers in the tray to separate fiber clumps;
wherein:
said tray is generally square or rectangular with two sides and two ends; and at least one baffle traversing the tray.

11. The method of claim 10, wherein the side walls comprise a wing angled inward from the sides, the wing comprising a slot to receive and support a baffle.

12. The method of claim 11, wherein the baffles are removable, and the baffles are inserted into the tray after the fiber slurry is introduced to the tray and manipulated.

13. The method of claim 10, wherein the tray is generally square shaped and is about 9-12 inches×9-12 inches.

14. The method of claim 11, wherein the wing has four shots and the tray has four removal baffles that are received and supported by the slots.

15. The method of claim 11, wherein two opposed side walls each have wings, and the baffle is supported by a slot on each wing.

16. The method of claim 10, wherein the tray and baffles are stainless steel.

17. The method of claim 10, wherein the fibers are centrifuged prior to the hydrating step.

18. The method of claim 10, wherein the fibers are frozen after manipulation in the tray, and the fibers are lyophilized after being frozen.

* * * * *